United States Patent
Lawrence et al.

(10) Patent No.: US 6,451,607 B1
(45) Date of Patent: Sep. 17, 2002

(54) EXTERNAL DRIED-REAGENT CONTROL FOR ANALYTICAL TEST DEVICES

(75) Inventors: Paul J. Lawrence, Campbell, CA (US); Robert Pena, San Jose, CA (US); Terrence J. Andreasen, San Jose, CA (US)

(73) Assignee: Litmus Concepts, Inc., Santa Clara, CA (US)

( * ) Notice: Subject to any disclaimer, the term of this patent is extended or adjusted under 35 U.S.C. 154(b) by 0 days.

(21) Appl. No.: 09/423,402

(22) PCT Filed: Apr. 4, 1999

(86) PCT No.: PCT/US99/08722
§ 371 (c)(1),
(2), (4) Date: Mar. 21, 2000

(87) PCT Pub. No.: WO99/57562
PCT Pub. Date: Nov. 11, 1999

Related U.S. Application Data

(63) Continuation-in-part of application No. 09/074,473, filed on May 7, 1998, now abandoned.

(51) Int. Cl.$^7$ ................................................. G01N 31/00
(52) U.S. Cl. ............................. 436/19; 436/8; 436/111; 436/163; 436/164; 422/61
(58) Field of Search ................................. 436/111, 163, 436/169, 165, 8, 11–15, 19, 180; 422/56, 58, 61

(56) References Cited

U.S. PATENT DOCUMENTS

| | | |
|---|---|---|
| 5,268,146 A | 12/1993 | Lawrence et al. |
| 5,416,003 A | 5/1995 | Lawrence et al. |
| 5,571,684 A | 11/1996 | Lawrence et al. |
| 5,585,273 A | 12/1996 | Lawrence et al. |
| 5,660,790 A | 8/1997 | Lawrence et al. |
| 5,885,526 A | 3/1999 | Chu |
| 5,897,834 A | 4/1999 | Lawrence et al. |
| 5,910,447 A | 6/1999 | Lawrence et al. |

*Primary Examiner*—Lyle A. Alexander
(74) *Attorney, Agent, or Firm*—Townsend and Townsend and Crew LLP

(57) ABSTRACT

A control device serving as a source of control reagent for a solid-phase analytical test device is disclosed. The analytical test device analyzes a biological sample for the presence of an analyte such as an enzyme or other chemical species or a particular pH range, and registers the presence or absence of the analyte as a detectable change in an indicator. The control device contains a control reagent that produces the same indicator change and that can be transferred to the analytical test device by a sample implement such as a wet swab. The control reagent is present on the control device as a dry lamina or combination of laminae. A positive control reagent on a control device in accordance with this invention mimics the action of the analyte once it is transferred to the analytical test device, while a negative control reagent on the control device mimics the action of a sample that lacks the analyte.

15 Claims, No Drawings

EXTERNAL DRIED-REAGENT CONTROL FOR ANALYTICAL TEST DEVICES

CROSS-REFERENCE TO RELATED APPLICATION

This application is a continuation-in-part of application Ser. No. 09/074,473, filed May 7, 1998, now abandoned, which was the National Sage of International Application No. PCT/US99/08722, filed Apr. 4, 1999 and hereby claims all benefits that are legally served thereby. The entire contents of application Ser. No. 09/074,473 are incorporated herein by reference.

BACKGROUND OF THE INVENTION

A variety of diagnostic tests for diseases and other biological conditions which utilize test products featuring built-in, specimen-activated control elements have been described in the patent literature. The purpose, utility and function of these control elements are described in U.S. Pat. Nos. 5,268,146, 5,416,003, 5,585,273, 5,571,684, and 5,660,790. All patents cited in this specification are incorporated herein by reference.

One example of a test product of this type is a self-contained test device designed to detect elevated pH and amines in vaginal fluid specimens (U.S. Pat. No. 5,660,790). The device features built-in, specimen-activated controls with an iconic readout of results. The readout is illustrated by a plus/minus sign, the positive test result being represented by a blue plus sign on a yellow background while the negative test result is represented by a blue minus sign on a yellow background. In this format, the horizontal bar generating the blue color (a yellow-to-blue color change) serves as the positive control while the non-color-changing yellow background serves as the negative control.

Another example is a self-contained test device for detection of proline iminopeptidase (PIP) activity in vaginal fluid, as disclosed in U.S. Pat. Nos. 5,268,146 and 5,571,684, again with built-in, specimen-activated controls. This device consists of a three-dimensional chamber which includes a test zone and positive and negative control zones. A positive test result is indicated by color formation (or change) in the test zone; a negative test result is indicated by the absence of color formation (or change) in the test zone. The positive control should form a color upon addition of a specimen, indicating that the indicator is indeed functioning, whereas the negative control zone should produce no such color, indicating that the device does not produce false positive results.

Products based on reporter enzyme release as described in U.S. Pat. Nos. 5,416,003 and 5,585,273 also feature built-in, specimen-activated positive and negative controls that serve purposes analogous to those of the built-in, specimen-activated positive and negative controls of the test devices of the preceding paragraphs.

The built-in, specimen-activated controls in these devices provide the user with assurance that each individual test device is in proper functioning condition. Because they are built into each device, these controls require no additional steps on the part of the user, and because they are activated by the specimen that is being tested, they can be true controls, ideally suited for this primary purpose.

Nonetheless, at least four additional factors suggest that additional value can be gained by providing dried controls, positive or negative, that are physically distinct from the test devices (i.e., separate devices) and that function independently of the built-in, specimen-activated controls:

(1) Appropriately formulated external controls can allow new users of the test device to see the appearance of a positive test result or a negative test result, prior to using the test device itself with clinical or other specimens, and thereby knowing what to expect or to look for in an actual test;

(2) Appropriately designed controls that are distinct from the test device and do not require specimen activation can provide a training opportunity for new users;

(3) The external controls can be included in a package of test devices, and the user can use the controls upon receipt of the entire package to ascertain that the materials in the test devices have not deteriorated during shipment; and (4) Physically distinct controls that do not require specimens for activation can permit more widespread use of the test device because they may facilitate regulatory approval for use by relatively untrained personnel.

To meet these objectives, the controls must not only function properly, but they must also be inexpensive and simple to use, and they must have a shelf life at least equal to, and storage requirements no greater than, those of the test device itself. Ideally, for a control device to serve as a training aid, the color produced by the control device should be stable over an extended period of time to permit observation and discussion among trainees. Most currently available external controls usually do not meet these requirements. For example, many current external controls consist of small bottles of positive and negative liquid control reagents that are expensive to manufacture, package, ship and store. Furthermore, such reagents often require refrigeration during storage. To apply liquid external controls to test kits, the user is often instructed to bring the refrigerated control solutions to room temperature before use, and to return them to refrigerated storage immediately after use. These requirements add to the complexity of test procedure. Because of these shortcomings, liquid controls are poorly suited to use with consumer products where instructive assistance is particularly important.

SUMMARY OF THE INVENTION

The present invention resides in a control device that is designed for use with any analytical test device, and particularly a solid-phase analytical test device, that is used for analysis of a liquid sample to detect the presence of an analyte in the sample by a detectable change in an indicator in the analytical test device. The control device is distinct from the analytical test device in that no sample is applied to the control device, no chemical reaction occurs in the control device, and no detection is made or test performed in the control device. Instead, the control device merely serves as a source of control reagent(s) to be used in the analytical test device. The control reagent(s) is a dry lamina (e) on the surface of the control device which itself is entirely solid and dry, and the reagent(s) can be removed by a wet swab or other implement and then transferred by the implement to the analytical test device. Once applied to the test device, the control reagent, if it is a positive control, causes a response identical to or analogous to that which would be caused by a sample that contains the analyte, and if the control reagent is a negative control, it causes a response identical or analogous to that which would be caused by a sample that does not contain the analyte. Use of the control device in this manner allows the user to determine whether or not the analytical test device is functioning properly, ie., whether an actual sample in which the analyte of interest is present would itself produce a positive reading on the analytical test device, or whether a sample that did not contain the analyte would produce a negative reading.

The control device of this invention is described herein by the terms "physically distinct" or "functionally distinct" relative to the analytical test device. These terms are intended to mean that the control device is not functionally joined to the analytical test device, i.e., the mere application of a liquid or a sample to one does not necessarily result in the application of the liquid or sample to the other. The two devices may be on a common base or substrate, and may or may not be separable from each other by cutting the substrate or breaking it along a scored line. Preferably, the two devices are on two distinct substrates that are not connected. In this separated arrangement, the control device is characterized in parts of this specification as "external" relative to the analytical test device. The control test reagents that are contained in the control device are likewise termed "external" to distinguish them from built-in specimen-activated control reagents or zones that are part of the analytical test device itself. The control test reagents are also referred to as "positive" and "negative" control reagents. The term "positive" in this context refers to a reagent which, when applied to the analytical test device, produces the same indicator response that would be produced if a sample containing the analyte were applied, the positive control reagent thereby serving to assure that the test device will function properly by producing a positive result when a sample containing the analyte of interest is applied. Likewise, the term "negative" in this context refers to a reagent which, when applied to the analytical test device, produces the same indicator response that a sample that does not contain the analyte is applied, the negative control reagent serving to assure that the test device will function properly when a negative sample is applied.

When the implement used to transfer the control reagent from the control device to the analytical test device is a wet swab, a wet sponge, or any other tool or medium that uses water, the dry positive control reagent is either water-soluble or sufficiently hydrophilic to permit the reagent to be lifted from the control device and transferred to the analytical test device. The control reagent will be chosen for a specific analytical test device, to induce the chemical reaction required in the analytical test device to achieve the indicator change. Depending on the methodology of the test device, the control reagent may therefore be identical, similar, or analogous to the analyte, which may itself be an enzyme, a particular small-molecule chemical species, an antigen or other binding partner, or a species with a high or low pH, for example. Alternatively, the control reagent may be identical, similar, or analogous to a component of the analytical test device that is released or activated by the analyte.

In cases where the control reagent mimics either the analyte or a component of the analytical test device, the control reagent may be the same as the species it is mimicking or a derivative or analog thereof that will function in the same or substantially the same manner. A derivative or analog may be preferable if it is more stable or more compatible with other components of the control device. In the case of a negative control, the control reagent will typically contain all the inert components of the positive control and only those components; i.e., the negative control would not contain the analyte or its analog.

In certain embodiments of the invention, the control device contains two or more control reagents (i.e., all positive control reagents or all negative control reagents), each for a separate test. All such control reagents will be in dry form and all will be transferable by a wet swab or other implement, and yet all will function independently. These embodiments are useful for analytical test devices that contain two or more different tests. In further embodiments of the invention, the dry laminae on the control device containing the control reagent(s) also contain pigments that serve to guide the user by showing where a control reagent is located and whether or not it has already been used. The typical pigment is inert and either accompanies the control reagent as the reagent is transferred or changes color when wetted. The pigmented laminae thus make it easier for the user to locate the laminae on the control device, and provide the user with assurance that the control reagents have been transferred to the swab. The pigments also help the user to differentiate a fresh control device with a full amount of control reagent from one that has already been used and depleted.

In the use of a control device of this invention, control reagent is lifted from the surface of the device and transferred to the analytical test device on which the control test is to be performed. Lifting and transferring is accomplished by any suitable transfer implement, examples of which are a swab, a sponge, a speculum, a pipette, or a dropper. With most of these implements, the reagent is preferably in wet form, i.e., either dissolved or suspended in a liquid solvent, preferably water, to facilitate the transfer. Since the control reagent is a dry lamina on the control device, the solvent can be introduced by the implement itself (a prewetted swab or sponge, or a liquid-filled dropper), or it can be applied first to the control device surface and the resulting liquid lifted from the device by the implement. In either case, the liquid and control reagent are then transferred together to the analytical test device.

These and other features, embodiments, advantages, and uses of the invention are explained in more detail below.

DETAILED DESCRIPTION OF THE INVENTION AND PREFERRED EMBODIMENTS

While this invention is susceptible of a wide range of implementations and embodiments, a detailed understanding of the invention as a whole can be gained by descriptions of specific embodiments. Accordingly, this section of the specification will focus on control devices for two particular analytical test devices -an elevated pH and volatile amine test card used for the diagnosis of bacterial vaginosis, as disclosed in U.S. Pat. No. 5,660,790 (Lawrence et al., issued Aug. 26, 1997, "pH and Amine Test Elements"); and a proline iminopeptidase test card for bacterial vaginosis, as disclosed in U.S. Pat. No. 5,571,684 (Lawrence et al., issued Nov. 5, 1996, "Assay for Proline Iminopeptidase and Other Hydrolytic Activities").

The elevated pH and volatile amine test card (which will be referred to herein as the "pH-amine test card") is a laminated device approximately the size of a common consumer credit card and contains two zones on its surface. The first is a pH test zone to detect pH equal to or greater than 4.7, containing an indicator that contains both an ionizable phenol group and a negatively charged group (such as a sulfate or sulfonate group), immobilized in a solid polymer matrix that contains quaternary ammonium groups. An example of an indicator of this description is nitrazine yellow, and illustrative polymers are ammonio methacrylate polymers and copolymers. The indicator and polymer are combined in a proportion that will provide the indicator with a transition point at pH 4.7. This combination of indicator and polymer occupy one geometrically defined surface region of the pH portion of the test card, while a second geometrically defined surface region is occupied by an indicator that has a transition point well below 4.7, for example 4.0 or below or preferably 3.5 or below. An example of an indicator of this type is a combination of nitrazine yellow and bromocresol green. A sample with a pH of less than 4.7 will thus produce a color change in the second region only while a sample with a pH of 4.7 or greater will produce a color change in both regions. If the second region is a bar arranged horizontally and the first region is a bar arranged vertically and crossing the horizontal bar, samples with pH below 4.7 will produce a "minus" sign (color change in the second region only) while sample with pH 4.7 or above will produce a "plus" sign (color change in both the first and second regions). An external negative control reagent in accordance with this invention will likewise produce the "minus" sign when applied to the pH portion of the test card, and an external positive control reagent will produce the "plus" sign.

The second test zone on the pH-amine test card is a test zone to detect the presence of volatilizable amines in the sample. The zone contains an indicator such as bromocresol green in a gas-permeable but liquid-impermeable matrix such as ethyl cellulose, plus a gaseous amine-releasing agent such as a solid alkali (sodium aluminate, for example). Thus, only those amines in the sample that are volatilized upon contact with the gaseous amine-releasing agent are able to produce a change in the indicator since only the gaseous amines can penetrate the matrix. This matrix occupies one geometrically defined region on the surface of the amine test portion of the card, while a second geometrically defined region is occupied by a different matrix, i.e., one that is both gas-permeable and liquid-permeable. Hydrophilic polymers, such as those used as matrices in the pH portion of the test card, will meet this description. The indicator in the second region can be the same as that used in the first region, and can be activated either by volatile or non-volatile amines or by the alkali used as the gaseous amine-releasing agent. As in the pH test, the second region can be a bar arranged horizontally while the first region is a bar arranged vertically and crossing the horizontal bar. A sample that does not contain amines that will be volatilized upon contact with sodium aluminate will produce a "minus" sign (color change in the second region only) while sample that does contain volatilizable amines will produce a "plus" sign (color change in both the first and second regions). An external negative control reagent in accordance with this invention will likewise produce the "minus" sign when applied to the amine portion of the test card, and an external positive control reagent will produce the "plus" sign.

The external positive and negative controls in accordance with this invention are not to be confused with the internal positive and negative controls that are included in the test device itself. As explained in U.S. Pat. No. 5,660,790, the internal positive and negative controls generally operate in a different manner, showing in an indirect way that the reagents are functioning but doing so without producing the same visual indication as a positive and a negative test result. By contrast with such internal controls, the external controls of the present invention mimic the positive and negative results in the test device by producing the same visual indication (for example, a plus sign for the positive result and a minus sign for the negative).

A preferred control device in accordance with this invention for the pH-amine test card is a single dried external positive or negative control device for testing both test elements of the pH-amine test card (i.e., controls for both the pH and amine test elements). The user simply rubs a wet swab over the dried control reagents, either individually or together, and performs the pH-amine test card tests according to the standard clinical instructions for using the pH-amine test card. The test result for each test element is preferably a color development which develops rapidly to intermediate intensity in both tests and is readily interpreted by novice users, the positive control producing a visual indication of a positive result (such as a plus sign) and the negative control producing a visual indication of a negative result (such as a minus sign). The control device should be as simple as possible to use and its effectiveness should be independent of the technique of the individual user.

For the pH test, an appropriate external positive control reagent will be any dried reagent that produces a pH substantially above 4.7, and preferably 5.0 or above, on the transfer implement used to transfer the reagent from the control device to the test card. In most cases, this will be a soluble acid, base or neutral species, optionally combined with an appropriate buffering agent. Examples of appropriate acids are 2-(N-morpholino)ethanesulfonic acid and citric acid, in solid, dry form. An appropriate external negative control will be any dried reagent that produces a pH substantially below 4.7 on the transfer implement. This reagent will in most cases be a soluble acid, optionally combined with an appropriate buffering agent, preferably one that maintains a pH less than 4.0, and most preferably less than 3.5. Other components that are preferably included in the positive control are a film forming agent to assist in the application of the control as a secure solid film to the surface of the control device, one or more detergents to enhance the wettability of the transfer implement with the control material and hence the ease of picking up the control by the implement and transferring it to the test device, and optionally other such components included for their physical properties but otherwise inert.

For the amine test, an appropriate external positive control will be any dried species that can be transferred by the transfer implement and that produces a volatile unprotonated amine when placed in contact with the gaseous amine-releasing agent on the test card. Examples of amines that meet this description are acid salts of primary amines, such as methylamine and diaminobutane. Likewise, an appropriate negative control will be any dried species that does not produce a volatile amine under the same circumstances. Like the other controls, the negative control may include a buffering agent, and may also include film formers, detergents, and other components to enhance the ability of the control reagent to form a film on the surface of the control device and to enhance the ability of the transfer implement to pick up the control and transfer it to the test device.

The preparation of dried control reagents or reagent laminae that are capable of meeting these performance goals and that meet the stability requirements and ease-of-use needs of the marketplace is accomplished by using materials with an appropriate balance of chemical properties. When an amine is used as the amine test positive control reagent, the amine control in its dry form on the control device should be maintained at a low pH to prevent oxidation and/or volatilization of the amine upon storage. This can be accomplished by using an acid salt of the amine. If the acid salt is present in excess, however, its acid content can partially or completely neutralize the alkali ring (the gaseous amine-releasing agent) surrounding the amine test element of the pH-amine test card, thereby interfering with the generation of the free, unprotonated amines that produce the color change in the amine test element. Conversely, the positive control reagent for the pH test should have a pH well above 4.7, and preferably in the range of approximately 5.0 to 7.0, to ensure credible, rapid color development in the pH test element on the pH-amine test card. Conversely, it has been found that high ionic strength is detrimental to color development of the pH element. Hence, preferred pH positive control reagents are those having a reasonably low ionic strength.

In embodiments of the invention in which the positive control reagents for both the pH test and the amine test are transferred simultaneously by the transfer implement and thus in contact on the implement, the two reagents should be formulated to eliminate or at least minimize any neutralizing or deactivating effect that either one may have on the other. For example, the amine test positive control reagent may be formulated to include a small amount of buffering agent to assure that when this reagent is combined with the pH test positive control reagent, the resulting pH is high enough to produce the positive result when applied to the pH portion of the test card. Likewise, if the combined positive control reagents have a pH that is too high, the amine components may deteriorate; whereas if the pH is too low (to stabilize the amine components), the pH control reagent may not produce a positive pH test result. Similarly, if the combined ionic strength of the two components is too high, the pH control may not function as desired, despite the pH of the formulation. These considerations will affect both the formulations of the control reagents and the choice of the manner in which they are arranged on the surface of the control device. In some cases, these considerations can be ameliorated by appropriate choice and combination of components for each formulation, and in other cases by selecting a geometrical or physical arrangement that will reduce the possibility of mixing or contact of the reagents before they are gathered by or absorbed into the transfer implement.

A preferred control device is one that contains dried, stable, functional positive controls for both test elements of the pH-amine test card, arranged in such a manner that both are picked up simultaneously by a single swab or other transfer implement and then both are applied simultaneously by the implement to first one test zone on the test card and then the other. This can be accomplished by placing all components for both pH and amine test elements in a single control reagent lamina or by placing them in individual, geometrically separated pH and amine control reagent laminae, zones or areas that are positioned sufficiently close to each other to permit the user to apply the transfer implement to all of the reagents substantially at the same time. Alternatively, the control test device can contain two independent dried external controls (ie., separate pH and amine controls, both positive or both negative) on separate locations of the device to be removed separately.

Single, combined reagent formats in the form of one or more identical, superimposed control reagent laminae, each containing all components needed to produce a positive response on both the pH and amine test elements, can thus be prepared. To perform the control test, the user rubs a wet swab over a designated area on the device, thereby transferring the control reagents which were deposited on that area to the swab. The swab is then used to apply the combined control reagents to both test elements (pH and amine) of the test card. Alternatively, the user can wet the control reagent area first and then rub a dry swab over the wet surface to pick up the control reagents. The single combined reagent (single lamina) approach has the advantage of simple manufacturing, but may in some cases (for the reasons given above) present challenges in formulating the reagent combination and in achieving long term stability if the individual control reagents have conflicting requirements.

A multiple laminar format, i.e., one in which individual controls are placed in separate and discrete laminae on the surface of the control device, can be prepared by using vertically or laterally separated laminae. In the pH and amine test example, the positive pH control reagent laminae may thus be placed in one lamina and the positive amine control reagent in another lamina. The term "vertically separated" or "vertically arranged" denotes distinct but superimposed laminae, one applied over the other, on the surface of the control device which is held in the horizontal position. The term "laterally separated" or "laterally arranged" denotes laminae or regions that are placed side-by-side in a non overlapping manner, and preferably separated by a small gap, on the surface of the device. One example of a geometric pattern of laterally separated laminae or regions is two halves of a circle in which one half is occupied by the pH positive control reagent and the other by the amine positive control reagent. Another example is a circle divided into quarter sections, where one of the two pairs of diagonally arranged sections is occupied by the pH positive control reagent and the other by the amine positive control reagent. A third example is two or more concentric rings where adjacent rings alternate in the control reagent occupying them. A fourth example is parallel strips where adjacent strips alternate between the pH control reagent and the amine control reagent. Other arrangements will be readily apparent to those skilled in the art.

To use the control device, the user mixes the laminae together with a wet clinical swab or other implement immediately prior to application to the test card to perform the control test. In the vertically separated arrangement the user rubs the swab over the uppermost lamina, drawing reagent from both laminae simultaneously. In the laterally separated arrangement, the user rubs the swab over the various regions using a circular or lateral sweeping motion, contacting each region. In either the vertical or lateral separation, both control reagents are mixed and picked up by the swab, then transferred to the pH-amine test card to perform control tests on the two test areas in succession. While these multiple laminar arrangements entail somewhat greater manufacturing complexity than a single laminar arrangement, they avoid the difficulties of incompatible control reagents and offer the potential benefit of utilizing two readily formulated reagents which interact minimally with each other until mixed by means of the swab.

Turing now to another example, the proline iminopeptidase ("PIP") test card is also a laminated device approximately the size of a common consumer credit card, the laminae forming an internal chamber with two opposing but non-contacting surfaces, one surface containing the conjugate L-proline-β-naphthylamide and the other containing the chromogenic indicator Fast Garnet GBC. When a sample containing proline iminopeptidase is placed in the chamber, the proline iminopeptidase cleaves the conjugate to release β-naphthylamine which migrates toward the indicator and changes its color. Referring to this chamber as the central chamber, the test card also contains two lateral chambers, one of which produces the same color change as the central chamber but does so regardless of whether or not the sample contains proline iminopeptidase. This is achieved by placing a solid non-volatile naphthylamine in the lateral chamber rather than the L-proline-β-naphthylamide, but also including the same indicator in the lateral chamber, the solid non-volatile naphthylamine being one that will dissolve in the sample and react with the indicator to produce the color change. An example of a naphthylamine meeting this description is 3-amino-2-naphthoic acid. Although the central and lateral chambers are joined by channels to permit the sample to enter both, the reagents remain in the respective chambers to differentiate the locations of the color changes.

A dried external positive control reagent in accordance with this invention for the PIP test card in accordance with this invention is preferably one that will contain the β-naphthylamine (or a similarly acting analog) in a form that is readily transferable by the transfer implement and once transferred will produce the indicator change in the central chamber, and yet prior to use will remain in dried form on the control device for an extended period of time until needed. β-Naphthylamine itself is volatile and slowly vaporizes. The positive control reagent should therefore be a naphthylamine derivative that remains firmly restrained within the dried control lamina until dissolved by a solvent (on a swab or other implement) and yet produces the color change in the indicator once it is dissolved and transferred. An example of such a derivative is a charged sodium salt of 3-amino-2-naphthoic acid. A lamina matrix that will stably retain this derivative is a quaternary amine polymer such as quaternized vinylpyrrolidone/dimethylaminoethyl methacrylate copolymer (GAFQUAT® 734, ISP Technologies, Inc., Bound Brook, N.J., USA) which holds the reagent within the lamina by ionic attraction. For a negative control, the lamina will contain only the quaternary amine polymer, plus any other components that may be included in the positive control other than the naphthylamine derivative.

As exemplified by the PIP test, some of the negative controls in accordance with this invention will not require a special reagent but instead simply the absence of the analyte or its analog to produce a negative indication on the test device. These negative controls should still be specially formulated to include all or substantially all of the reagents of the positive control other than the analyte or analyte analog, to assure a consistent and reliable result. For example, where water alone could produce the negative indication in the test device, a properly formulated negative control avoids the disadvantages of the variable ion composition, ionic strength and pH of tap water, while offering the advantage of the same consistency, appearance and procedure of use of the positive control. Thus, the negative control may contain buffering agents, film forming agents, and detergents, where these components are also present in the positive control. These components will therefore serve as the negative control reagent.

Whether the control device is designed for use on a pH-amine test card, a PIP test card, or on any other type of analytical test device, and whether the control reagents on the control device are single laminae or multiple laminae, vertically separated or laterally separated, certain additional features will often be useful. For example, when the control reagent laminae are colorless or nearly colorless, the user may find it useful if some means is provided to make the control reagent laminae readily visible on the control test device, the swab, or both.

One means of achieving this is to use a control device whose underlying base is strongly colored and/or shiny. The control reagent laminae can be made to appear as semiopaque or to have a milky appearance, and its removal from the shiny, colored surface of the device will be readily apparent.

Another means of making the control reagent(s) visible is to incorporate an inert dye or pigment into the control zone. The colored area thus shows the user where to apply the swab (or other implement). The user can also determine whether the reagent has been picked up by the implement by examining the surface of the device for removal of the colored area or by examining the implement itself. Laminar pigmentation can be achieved by adding a dye or pigment to one or more of the reagent laminae, or by depositing one or more chemically inert dye or pigment laminae beneath or above the control reagent laminae. A further means of making the control reagent(s) visible and confirming whether or not they have been used is to use colored laminae that change color upon contact with the transfer solvent. This can be accomplished with a suitable pH indicator. The dyes, pigments, or other coloring agents can be chosen and tested specifically to assure that they will present no interference with the control reagents themselves. The quantities and color of the dyes, pigments, or coloring agents would also be chosen to assure that there will be no interference with the color change in the test zone on the analytical test device, and to have no effect on reagent stability.

An alternative to the use of dyes, pigments, or coloring agents is the incorporation of highly colored polymeric microparticles into one or more control reagent laminae or into a top or bottom lamina (i.e., above or below the control reagent). Microparticles with coloring agent imbedded inside them during their formation are known in the art. The coloring agent in these microparticles will not directly contact the control reagents, even when both are retained on a single swab. These microparticles are highly inert and tend to adhere to clinical swabs, thereby transferring little or no color to the analytical test device.

Regardless of their configuration or chemistry, the control test devices of this invention will generally contain indicia such as drawings, illustrations, or text, instructing the user as to the appropriate methods of use.

In manufacturing a control test device in accordance with this invention, the control reagent(s) is applied to a solid base or support in a conventional manner to form a lamina or laminae on the surface of the base. When there are constraints on the concentration of the reagent in the formulation being applied, it may be necessary to apply multiple laminae superimposed to achieve the desired amount of reagent. When laterally separated laminae are applied, the geometric patterns can vary considerably and are not critical. For example, distinct reagents can be applied side-by-side as two halves of a circle, as a series of concentric rings, or as alternating strips. When vertically arranged (superimposed) laminae are applied, particularly when one lamina contains a different control reagent than the one directly above or below it, one can avoid mixing of the reagents during formation of the laminae by using different, incompatible or immiscible solvents for the formulations used to form each lamina. Combinations of laterally and vertically separated laminae can also be used.

The following examples are offered only for purposes of illustration.

EXAMPLE 1

This example illustrates the preparation and use of various positive control materials, including liquid solutions and solid devices with dried reagent laminae, for a test device for pH and volatile amines used for the diagnosis of vaginal infections, as described in U.S. Pat. No. 5,660,790. The various positive control devices contained different configurations and arrangements of the reagents, forming both individual and combined pH and amine reagent solutions for use as the positive controls.

Materials
- 2-(N-Morpholino)ethanesulfonic acid ("Mes") free acid
- 2-(N-Morpholino)ethanesulfonic acid ("Mes") sodium salt
- Sorbitol (70% solution)
- Hydroxypropylcellulose
- Maltodextrin M040
- Deionized water
- Methylamine (hydrochloride)

All formulations were prepared on a weight/weight basis:

FORMULATION #1—pH test control reagent
- 20 mM Mes (free acid)
- 180 mM Mes (Na salt)
- 7.00% sorbitol
- 6.00% hydroxypropylcellulose
- balance: deionized water
- pH=7.2

FORMULATION #2—amine test control reagent
- 50 mM Mes (free acid)
- 200 mM methylamine hydrochloride
- 7.00% sorbitol
- 6.00% hydroxypropylcellulose
- balance deionized water
- pH=4.4

FORMULATION #3—pH test control reagent
- 20 mM Mes (free acid)
- 180 mM Mes (Na salt)
- 8.00% maltodextrin M040
- 7.00% sorbitol
- 6.00% HPC
- balance: deionized water
- pH=7.2

FORMULATION #4—amine test control reagent
- 50 mM Mes (free acid)
- 200 mM methylamine hydrochloride
- 8.00% maltodextrin M040
- 7.00% sorbitol
- 6.00% hydroxypropylcellulose
- balance: deionized water
- pH=4.4

Procedures

Test devices for pH and volatile amines were assembled as described in U.S. Pat. No. 5,660,790. Briefly, each test device contained two test elements or test zones: the first test element or test zone (the pH test element) produces a color change from yellow to blue when exposed to a solution of pH≧4.7; the second test element or test zone (the amine test element) produces a color change from yellow to blue when exposed to a solution containing alkali-volatilizable amines. In the presence of a solution with a pH<4.7, no color change is produced in the pH test zone or test element. Similarly, in the presence of a solution which does not contain volatilizable amines, no color change is produced in the amine test element or test zone. These test devices are operated by wetting a standard clinical swab with the test solution and rubbing the wetted swab directly on the test zones of the test device. The pH test element on each test device contained nitrazine yellow as an indicator, immobilized in a matrix of an ammonio methacrylate copolymer. The amine test element on each test device contained bromocresol green indicator in an ethyl cellulose matrix surrounded by a ring of sodium aluminate to release gaseous amines from the control reagent. The standard procedure for the pH test element was to rub a sample-moistened swab over the test element surface and observe the color change if any, while the standard procedure for the amine test element was to rub a sample-moistened swab first over the sodium aluminate ring and then over the region containing the bromocresol green indicator, and then to observe any color change in the indicator.

To test individual control solutions as external positive controls representative of the present invention, two drops of each formulation were added to the tip of a swab and the swab was then rubbed in a circular fashion over the appropriate test zone on the pH-amine test device. Formulations 1 and 3 were applied to the pH test zone and Formulations 2 and 4 to the amine test zone of the test device. After approximately 1 minute, the color intensities in the test zones were recorded.

To test combinations of control solutions, the combinations were made by mixing equal volumes of Formulation 1 and Formulation 2 (final pH=6.55) or Formulation 3 and Formulation 4 (final pH=6.50). Two drops of each mixture were added to the tip of a swab and the swab was then rubbed in a circular fashion over both test zones on the test device. After approximately 1 minute, the color intensities in the test zones were recorded.

Control devices containing either dried pH test or dried amine test control laminae were prepared as follows. Approximately 5 mL of the liquid formulation of the control reagent was added to a standard ink proofing roller. The roller was then carefully guided over the surface of a sheet of 10 mil MYLAR®, and the resulting thin wet coating was dried with a heat gun.

Control devices containing a single dried lamina containing both pH and amine test control reagents were prepared as follows. Approximately 5 mL of a mixture of Formulations 1 and 2 or a mixture of Formulations 3 and 4 were added to a standard ink proofing roller. The roller was then carefully guided over the surface of a sheet of 10 mil MYLAR®, and the resulting thin wet coating was dried with a heat gun.

The following procedures were used to prepare control devices containing multiple dried laminae of either pH or amine test control reagents.

Control Device 1: laterally separated pH and amine control reagent laminae: Individual dried laminae prepared from Formulation 1 and Formulation 2 were prepared as indicated above, except that to produce laterally separated laminae of the pH and amine control reagents, the pH and amine laminae were deposited side-by-side on a single MYLAR® sheet with the laminae separated from each other by a very narrow gap (approximately 0.1 inch (0.25 cm)).

Control Device 2: laterally separated pH and amine control reagent laminae: The procedure was the same as that for Control Device 1, except that Formulations 3 and 4 were used in place of Formulations 1 and 2, respectively.

Control Device 3: vertically separated single pH and amine control reagent laminae: A first dried lamina prepared from pH Formulation 1 was applied as described above. A second dried laminae containing amine Formulation 2 was then deposited directly over the first dried lamina. The resulting device consisted of a lower lamina containing a dried pH positive control reagent and an upper lamina containing a dried amine positive control reagent.

Control Device 4: vertically separated single pH and amine control reagent laminae: The procedure was the same as that for Control Device 3, except that Formulations 3 and 4 were used in place of Formulations 1 and 2, respectively.

Control Device 5: vertically separated single pH and amine control reagent laminae: The procedure was the same as that for Control Device 3, except that Formulation 2 (an amine control reagent) was used as the lower lamina and Formulation 1 (a pH control reagent) as the upper lamina.

Control Device 6: vertically separated single pH and amine control reagent laminae: The procedure was the same as that for Control Device 5, except that Formulation 3 (an amine control reagent) was used as the lower lanina and Formulation 4 (a pH control reagent) as the upper lamina.

Single-laminate control devices were tested as follows. To define a dried laminar reagent zone on the MYLAR® sheet, a circular area approximately $3/8^{th}$ inch (0.95 cm) in diameter was created on the laminar surface of each device by adhering a strip of adhesive tape onto the laminar surface of each device over the dry reagent coating. The adhesive tape contained a $3/8^{th}$-inch hole which thereby exposed a defined circular area of the device surface. To test the performance of the single-laminate devices, two drops of deionized water were added to a standard cotton clinical swab, and the wet swab was rotated over the exposed circular area of the laminar surface created by the hole in the adhesive tape several times to remove the lamina from the device. The swab was then used to perform the appropriate (i e., either pH or amine) test.

Multi-laminate control devices were tested as follows. To define a dried laminar reagent zone on the MYLAR® sheet, a circular area approximately $3/8^{th}$ inch (0.95 cm) in diameter was created on the laminar surface of each device accomplished by adhering a strip of adhesive tape onto the laminar surface of each device over the dry reagent coating. The adhesive tape contained a $3/8^{th}$-inch (0.95-cm) hole which thereby exposed a defined circular area of the device surface. In the laterally separated multi-laminate devices, this hole was located on the laminar surface of the device such that the circular area exposed portions of each lamina (half of the exposed area lay within the pH reagent lamina while the other half lay within the amine reagent lamina). To test the performance of the devices containing two laterally separated positive control laminae, two drops of deionized water were added to a standard cotton clinical swab, and the wet swab was rotated over the exposed circular area created by the hole in the adhesive tape several times to remove both reagents from the device. The swab was then used to perform the pH and amine tests.

For vertically separated multi-laminate devices, an adhesive strip containing a circular hole to expose a circular area of the uppermost reagent lamina.

Stability testing: Each of Control Devices 1 through 6 was used with an individual pH and amine test device immediately after preparation of the control device, and the results in terms of the color changes on the pH-amine test device were immediately observed. Fresh Control Devices 1 through 6 were then heat sealed in aluminum foil pouches (foil/poly bags from Aldrich Chemical Company), each pouch containing 1.0 gram silica gel desiccant containers (SORBIT from United Desiccators), and stored at a controlled temperature of 45° C. for a specified time interval. After this interval, the control devices were removed from their protective pouches, applied to fresh pH-amine test devices, and the results in terms of the color changes on the pH-amine test device were again observed. The color changes are listed in Tables 1A through 1C, where the "immediate" results represent those taken immediately after the control devices were prepared, and the "heat stressed" results represent those taken after storage of the control devices at 45° C., with the duration of storage shown in parentheses.

| Legend: | NA = not appropriate |
| --- | --- |
| | ND = not done (test not performed) |
| Color Score System: | 0 = no detectable color on pH-amine test device |
| | 0.5 = lowest color intensity |
| | 1.5 = low-to-intermediate color intensity |
| | 2.5 = to-intermediate color intensity |
| | 5.0 = extremely high color intensity |

TABLE 1A

Test Results (Color Scores on pH-Amine Test Device) Using Liquid Control Reagents

| | pH Test | | Amine Test | |
| --- | --- | --- | --- | --- |
| Formulation(s) | Immediate | Heat Stressed | Immediate | Heat Stressed |
| 1 | 3 | ND | NA | ND |
| 3 | 3 | ND | NA | ND |
| 2 | NA | ND | 3 | ND |
| 4 | NA | ND | 3 | ND |
| 1 & 2 | 3 | ND | 3 | ND |
| 3 & 4 | 3 | ND | 3 | ND |

TABLE 1B

Test Results (Color Scores on pH-Amine Test Device) Using Single-Laminate Dried Control Reagents

| | pH Test | | Amine Test | |
| --- | --- | --- | --- | --- |
| Formulation(s) | Immediate | Heat Stressed (24 hours) | Immediate | Heat Stressed (24 hours) |
| 1 | 3 | 3 | NA | NA |
| 3 | 3 | 3 | NA | NA |
| 2 | NA | NA | 3 | 3 |
| 4 | NA | NA | 3 | 3 |
| 1 & 2 | 3 | 1.5 | 3 | 1 |
| 3 & 4 | 3 | 1.5 | 3 | 1 |

TABLE 1C

Test Results (Color Scores on pH-Amine Test Device) Using Multi-Laminate Dried Control Reagents

| | pH Test | | Amine Test | |
| --- | --- | --- | --- | --- |
| Formulation(s) | Immediate | Heat Stressed (8 days) | Immediate | Heat Stressed (8 days) |
| 1 | 3 | 3 | 3 | 3 |
| 2 | 3 | 3 | 3 | 3 |
| 3 | 3 | 0.5 | 3 | 2 |
| 4 | 3 | 0.5 | 3 | 3 |
| 5 | 3 | 3 | 3 | 0.5 |
| 6 | 3 | 3 | 3 | 0.5 |

These test results demonstrate that:

1. Liquid control reagents can be deposited on a solid MYLAR® support as individual thin, dry, laminae to produce a functioning positive external control device for the pH-amine test card.

2. A mixture prepared by mixing equal volumes of the liquid pH and amine positive controls can be deposited as a thin, dry lamina to produce a functioning external positive control device for both test elements of the pH and amine test card. A combination device prepared in this manner simulated the performance of vaginal fluid specimens, and provides an added advantage of convenience.

3. Discrete laminae that are either laterally or vertically separated and contain a pH reagent positive control and an amine positive control reagent, respectively, perform acceptably as external positive controls for the pH-amine test card.

EXAMPLE 2

This example illustrates the preparation and use of additional individual and combined pH and amine reagent solutions as external positive controls for a pH-amine test device identical to that used in Example 1. The utility of these individual and combined solutions in forming functional, dried reagent laminae capable of serving an external positive control devices for the test device is also illustrated. The effect of lateral laminae separation on positive control device performance with the test device and the effect of heat stress on the performance and stability of dried external control devices are also illustrated.

Materials

Sodium citrate, dihydrate

Citric acid, monohydrate

Poly(ethylenimine)

Hydroxypropylcellulose 1,4-Diaminobutane, dihydrochloride (putrescine)

1,5-Diaminopentane, dihydrochloride (cadaverine)

Deionized water

All formulations were prepared on a weight/weight basis:

FORMULATION #1—amine test control reagent 0.30% citric acid, monohydrate 1.05% sodium citrate, dihydrate 8.00% hydroxypropylcellulose 12.00% 1,4-diaminobutane dihydrochloride (putrescine)

balance: deionized water pH=12.3

FORMULATION #2—amine test control reagent 0.30% citric acid, monohydrate 1.05% sodium citrate, dihydrate 8.00% hydroxypropylcellulose 12.00% 1,5-diaminopentane, dihydrochloride (cadaverine)

balance: deionized Water pH=4.4

FORMULATION #3—pH test control reagent 0.30% citric acid, monohydrate 1.05% sodium citrate, dihydrate 8.00% hydroxypropylcellulose 1.25% poly(ethylenimine)

balance: deionized water pH=8.70

Procedures

The procedures for testing individual external liquid positive control solutions, combined external liquid positive control solutions, and positive control devices containing either dried pH or dried amine control laminae were the same as those described above in Example 1. Positive control devices containing multiple dried laminae of either pH or amine control reagents were prepared as described below.

Control Device 1: laterally separated pH and amine (putrescine) laminae: Individual dried laminae prepared from Formulation 1 and Formulation 2 were prepared as indicated above, except that pH and amine control reagent laminae were deposited side-by-side on a single MYLAR® sheet with the laminae separated from each other by a very narrow gap (approximately 0.1 inch).

Control Device 2: laterally separated pH and amine (cadaverine) laminae: This device was prepared in the same manner as Control Device 1, except that Formulation 3 and Formulation 4 were used in place of Formulation 1 and Formulation 2, respectively.

Control Device 3: laterally separated multiple pH and amine (putrescine) laminae: Two superimposed dried laminae prepared from Formulation 1 and two superimposed dried laminae prepared from Formulation 3 were prepared by sequentially depositing the laminae side-by-side on the same MYLAR® surface. The double laminae were separated by a very narrow gap (approximately 0.1 inch), with the Formulation 1 laminae on one side of the gap and the Formulation 3 laminae on the other.

Control Device 4: laterally separated multiple pH and amine (cadaverine) laminae: This device was prepared in the same manner as Control Device 3 except that Formulations 2 and 3 were used in place of Formulations 1 and 3, respectively.

Control Device 5: vertically separated single pH and amine (putrescine) laminae: A first dried lamina prepared from pH Formulation 3 was prepared as described above. A second dried lamina containing amine Formulation 2 was then deposited directly over the first dried lamina. The resulting device consisted of a lower lamina containing a dried pH positive control reagent and an upper lamina containing a dried amine positive control reagent.

Control Device 6: vertically separated single pH and amine (cadaverine) laminae: A first dried lamina prepared from pH Formulation 3 was prepared as described above. A second dried lamina containing amine Formulation 4 was deposited directly over this first dried lamina. The resulting device thus contained a lower lamina containing a dried pH positive control reagent and an upper lamina containing a dried amine positive control reagent.

Control Device 7: vertically separated single pH and multiple amine (putrescine) laminae: A first dried lamina prepared from pH Formulation 3 was prepared as described above. A second dried laminae containing amine Formulation 1 was deposited directly over the first dried lamina, and a third dried lamina containing amine Formulation 1 was deposited over the two underlying laminae. The resulting device contained a lower dried lamina containing a dried pH positive control reagent and two upper dried laminae containing amine positive control reagents.

Control Device 8: vertically separated single pH and multiple amine (cadaverine) laminae: A first dried lamina prepared from pH Formulation 3 was prepared as described above. A second dried lamina containing amine Formulation 2 was deposited directly over the first dried lamina, and a third dried lamina containing amine Formulation 2 was deposited over the two underlying laminae. The resulting device consisted of a lower dried lamina containing a pH positive control reagent and two upper dried laminae containing amine positive control reagents.

Circular areas of the dried reagent laminae on each of the various devices were defined and exposed as in Example 1, using adhesive strips with circular holes. Stability tests were likewise performed in the manner described in Example 1. The results are listed in Tables 2A through 2C, using the same legend and color score system as in Example 1.

TABLE 2A

Test Results (Color Scores on pH-Amine Test Device)
Using Liquid Control Reagents

| | pH Test | | Amine Test | |
|---|---|---|---|---|
| Formulation(s) | Immediate | Heat Stressed | Immediate | Heat Stressed |
| 1 | NA | ND | 5 | ND |
| 2 | NA | ND | 5 | ND |
| 3 | 4 | ND | NA | ND |
| 1 & 3 | ND | ND | ND | ND |
| 2 & 3 | ND | ND | ND | ND |

TABLE 2B

Test Results (Color Scores on pH-Amine Test Device)
Using Single-Laminate Dried Control Reagents

| | pH Test | | Amine Test | |
|---|---|---|---|---|
| Formulation(s) | Immediate | Heat Stressed | Immediate | Heat Stressed |
| 1 | NA | ND | 2.0 | ND |
| 2 | NA | ND | 2.0 | ND |
| 3 | 3.0 | ND | NA | ND |

TABLE 2C

Test Results (Color Scores on pH-Amine Test Device)
Using Multi-Laminate Dried Control Reagents

| | pH Test | | Amine Test | |
|---|---|---|---|---|
| Formulation(s) | Immediate | Heat Stressed (60 days) | Immediate | Heat Stressed (8 days) |
| 1 | 3 | ND | 1.5 | ND |
| 2 | 3 | ND | 1.5 | ND |
| 3 | 3 | ND | 1.5 | ND |
| 4 | 3 | ND | 1.5 | ND |
| 5 | 3 | ND | 1.5 | ND |
| 6 | 3 | ND | 1.5 | ND |
| 7 | 2.5 | 2.5 | 2.5 | 2.0 |
| 8 | 2.5 | 2.5 | 2.5 | 2.0 |

These test results demonstrate that a successful liquid positive control reagent for the pH test can be prepared from a citrate-base pH reagent, and successful liquid positive control reagents for the amine test can be prepared from two separate diamine reagents, putrescine and cadaverine. Moreover, these reagents can be deposited as individual thin, dry laminae on the surface of the control device. There was no significant difference between the performance of putrescine and that of cadaverine. Mixtures of equal volumes of the pH and amine liquid control reagents used in this example however did not result in a material capable of being deposited on the control device surface. For vertically or laterally separated laminae of the dried pH and amine control reagents, best results were obtained with one pH control lamina and two amine control laminae.

EXAMPLE 3

This example illustrates the use of coloring agents with dried control reagents on a control device for use with the same pH-amine test card addressed by Examples 1 and 2. This example also illustrates the use of alternative procedures for using the control devices.

Materials 2-(N-Morpholino)ethanesulfonic acid ("Mes") free acid 2-(N-Morpholino)ethanesulfonic acid ("Mes") sodium salt Sorbitol (70% solution)

Hydroxypropylcellulose

Maltodextrin M040

Deionized water

Methylamine (Hydrochloride)

PL-Latex SUPER CARBOXYL Hi Dye 370 nm (red) or 814 nm (blue) microparticulate dye suspensions, from Polymer Laboratories FORMULATION #1—pH test control reagent 20 mM Mes (free acid)

270 mM Mes (Na salt)

8.00% Maltodextrin M040

7.00% sorbitol 6.00% hydroxypropylcellulose balance: deionized water pH=7.2

FORMULATION #2—amine test control reagent 75 mM Mes (free acid)

300 mM methylamine hydrochloride 8.00% Maltodextrin M040

7.00% sorbitol 6.00% hydroxypropylcellulose balance: deionized water pH=3.2

Procedures

The procedures for preparing and testing positive control devices containing either a dried pH test control lamina or a dried amine test control lamina, and for positive control devices containing multiple dried laminae consisting of laterally separated pH test and amine test control laminae were the same as those described above in Example 1. In the devices with the laterally separated laminae, the pH control lamina was red and the amine control lamina was blue. To test the performance of the control devices containing these red and blue laterally separated control laminae, two distinct application procedures were employed:

(1) In the first procedure, one or two drops of deionized water were added to a standard cotton clinical swab, and the wet swab rotated over the exposed circular area created by the hole in the adhesive tape several times to remove both colored laminae from the control device surface. The swab was then applied to both test areas on the pH-amine test card.

(2) In the second procedure, one or two drops of deionized water were added to the circular area of the two-colored laminate surface of the control device. A standard cotton clinical swab was then rotated over the surface to remove both colored laminae. The swab was then applied to both test areas on the pH-amine test card.

Results and Observations (1) The red pH lamina and the blue amine lamina in the control device were clearly visible to the user, appearing as a circle on the dried control device, one half of the circle being red and the other blue.

(2) When a pre-wetted swab was rotated over the dual colored control device according to application procedure no. 1, the colored laminae were removed from the device as evidenced by the absence of color on the device. Similarly, transfer of the color from the device to the wet swab tip was clearly visible by the formation of a purple color on the swab tip itself. The color on the swab tip was obviously a combination of colors in the two control reagent laminae.

(3) When a drop of water was added to the dried positive control device, and a dry swab used to remove the laminae from the device according to application procedure no. 2, the observations cited in the preceding paragraph were again made.

(4) When a swab containing the colored components obtained by using either test procedure was used to perform both the pH and the amine test on the pH-amine test card, both tests produced a color score of 3 (using the color score definitions of Example 1).

(5) The dye particles picked up by a clinical swab remained essentially bound to the swab after the pH and amine tests were performed on the pH-amine test card. Hence, despite the presence of clearly visible colored particles on the swabs, no interference in the pH-amine test card performance or interpretation was seen.

EXAMPLE 4

This example illustrates the preparation and use of a control device containing a dried control reagent lamina for use with a test device for proline iminopeptidase (PIP) as described in U.S. Pat. No. 5,571,684. This device is an enclosed chamber with upper and lower inside surfaces (i. e., a ceiling and floor); immobilized on the floor is the conjugate L-prolyl-β-naphthylamide, and immobilized on the ceiling is dried Fast Garnet GBC chromogenic indicator. When a liquid sample containing PIP is placed inside the test device, the conjugate on the floor is cleaved to release β-naphthylamine, which then migrates to the ceiling where it causes a color change in the indicator. Two types of test device described in U.S. Pat. No. 5,571,684 were used—a device in which the ceiling and floor are separated by an open space (the "well" format), and a device in which the space between the ceiling and floor is occupied by a liquid-penetrable fiber (the "fiber" format). A positive test result in either type of PIP test device is indicated by the formation of a red color in the indicator.

Materials

Sodium 3-amino-2-naphthoate (SAM)
Quaternized vinylpyrrolidone/dimethylaminoethyl methacrylate copolymer (GAFQUAT® 734)
Methanol
Deionized water Formulation (All Percentages on a Weight/weight Basis)

50 mM SAM
22% GAFQUAT® 734
38% Methanol
40% Deionized water

To prepare the control devices, approximately 5 mL of the Formulation were added to a standard proofing roller. The roller was carefully guided over the surface of a sheet of 10 mil MYLAR®, and the resulting thin wet coating was dried with a heat gun. Circles (0.5 inch in diameter) of the MYLAR® support containing the SAM lamina were punched from the sheet and affixed to an adhesive surface with the SAM lamina facing upward (exposed).

Two test methods were used to test the control devices:

(1) One to five drops of deionized water (approximately 40 microliters/drop) were added to the dried SAM lamina on the control device surface. A dry DACRON® swab was rubbed on the wetted lamina surface for 5 seconds using a circular motion, thereby wetting the swab and simultaneously transferring the control reagent to the swab. The swab thus wetted was then used to apply the control reagent to the PIP test device.

(2) This method was identical to the first method, except that the drops of deionized water were added to a dry DACRON® swab, which was then rubbed on the dried SAM lamina on the control device surface. The wetted swab was then used to apply the control reagent to the PIP test device.

For the "well" format PIP test device, the wet swab was rolled against the opening in the top of the device, expressing liquid into the device receptacle. For the "fiber" format PIP test device, the wet swab was simply touched to the porous solid support, and the liquid was absorbed directly into the test device.

The results are listed in Table 3.

TABLE 3

Test Results With Positive Control on PIP Test Device

| PIP Test Device Format | Drops of Water Added | Water Added To: | PIP Test Color | Comments |
|---|---|---|---|---|
| well | 3 | SAM lamina | none | |
| well | 4 | SAM lamina | none | |
| well | 5 | SAM lamina | red | Red color over entire top of device |
| well | 4 | swab | none | |
| well | 5 | swab | none | |
| fiber | 2 | SAM lamina | red | Small, red test zone |
| fiber | 3 | SAM lamina | red | Medium sized, red test zone |
| fiber | 4 | SAM lamina | red | Large, red completely filled test zone |
| fiber | 3 | swab | red | Medium sized, red test zone |
| fiber | 4 | swab | red | Medium-to-large red test zone |

These results indicate that a thin, dry lamina containing SAM can serve as a functional positive control for the PIP test device in both the well format and the fiber format, and that both methods of transferring the SAM to the test device were effective.

The foregoing is offered primarily for purposes of illustration. It will be readily apparent to those skilled in the art that the operating conditions, materials, procedural steps, geometrical arrangements and other parameters of the embodiments described herein may be further modified or substituted in various ways without departing from the spirit and scope of the invention.

What is claimed is:

1. A control device for use in performing a positive control test of a solid-phase analytical test device, said solid-phase analytical test device being one that comprises an indicator and that detects the presence of an analyte in a liquid sample by a change in said indicator, said control device comprising:

a solid support having a dry control reagent adhering thereto and no components that are chemically reactive with said control reagent, said reagent being arranged on said solid support in a manner permitting removal of said reagent from said support by a wet transfer implement which is either a swab or a sponge, and said reagent being either water-soluble or sufficiently hydrophilic to cause said reagent to be transferred to said wet transfer implement upon contact of said wet transfer implement to said reagent, said reagent being selected as one which when applied to said test device by said wet transfer implement causes an indicator change that is substantially the same as that which occurs in the presence of said analyte.

2. A control device in accordance with claim 1, in which said dry control reagent is a member selected from the group consisting of said analyte and chemical derivatives thereof that function in substantially the same manner in said solid-phase test device as said analyte.

3. A control device in accordance with claim 1, in which:
(a) said analytical test device contains a chemical species that is released by said analyte and thus released produces a change in said indicator, and
(b) said dry control reagent is a member selected from the group consisting of said chemical species and chemical derivatives thereof that function in substantially the same manner in said analytical test device as said chemical species.

4. A control device in accordance with claim 1, comprising a plurality of dry control reagents adhering to said solid support, each of said reagents corresponding to a different test among a plurality of tests on said analytical test device for detection of a plurality of analytes, such that a transfer implement bearing said plurality of reagents when applied to said test device causes an indicator change in each of said tests that is substantially the same as those that occur in the presence of said analytes.

5. A control device in accordance with claim 4 in which said plurality of dried control reagents is combined as a mixture in a single solid composition.

6. A control device in accordance with claim 4 in which each member of said plurality of dried control reagents is contained in a separate solid composition, thereby forming a plurality of solid compositions arranged in spatially distinct locations on said control device.

7. A control device in accordance with claim 6 in which said spatially distinct solid compositions are laterally arranged on the surface of said solid support.

8. A control device in accordance with claim 6 in which said spatially distinct solid compositions are vertically arranged on the surface of said solid support.

9. A control device in accordance with claim 1 in which said analyte is a species that imparts to said sample a pH exceeding 4.7, said indicator is a compound containing an ionizable phenol group and a negatively charged group dispersed in a polymer containing quaternary ammonium groups, and said dry control reagent is an acid having a pH greater than 5.0.

10. A control device in accordance with claim 9 in which said dry control reagent is a member selected from the group consisting of 2-(N-morpholino)ethanesulfonic acid and citric acid.

11. A control device in accordance with claim 1 in which said analyte is a species that releases a volatile amine when placed in said solid-phase test device, said indicator is a substance that undergoes a visual change when contacted with a volatile amine, and said dry control reagent is an acid salt of an amine.

12. A control device in accordance with claim 11 in which said acid salt of an amine is a member selected from acid salts of methylamine and diaminobutane.

13. A control device in accordance with claim 3 in which said chemical species is β-naphthylamine, said solid-phase analytical test device comprises a conjugate of β-naphthylamine, said analyte is an enzyme that cleaves said conjugate to release said β-naphthylamine, said indicator is a compound that undergoes a color change when contacted with β-naphthylamine thus released, and said dry control reagent is a nonvolatile naphthylamine derivative that produces said color change in said indicator.

14. A control device in accordance with claim 13 in which said non-volatile naphthylamine derivative is 3-amino-2-naphthoic acid dispersed in a quaternary amine polymer.

15. A control device for use in performing a negative control test of a solid-phase analytical test device, said solid-phase analytical test device being one that comprises an indicator and that detects the absence of an analyte by a first change in said indicator and the presence of said analyte by a second change in said indicator, said control device comprising:

a solid support having a dry control reagent adhering thereto and no components that are chemically reactive with said control reagent, said reagent being arranged on said solid support in a manner permitting removal of said reagent from said support by a wet transfer implement which is either a swab or a sponge, and said reagent being either water-soluble or sufficiently hydrophilic to cause said reagent to be transferred to said wet transfer implement upon contact of said wet transfer implement to said reagent, said reagent being selected as one which when applied to said test device by said wet transfer implement causes an indicator change that is substantially the same as said first change.

* * * * *